(12) United States Patent
Pereira et al.

(10) Patent No.: US 11,684,358 B2
(45) Date of Patent: Jun. 27, 2023

(54) FUSIBLE BIODEGRADABLE SUTURES UTILIZING TISSUE SOLDERING TECHNOLOGY

(71) Applicant: Boston Scientific Scimed, Inc., Maple Grove, MN (US)

(72) Inventors: Peter J. Pereira, Mendon, MA (US); Jonathan Zoll, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 563 days.

(21) Appl. No.: 15/083,845

(22) Filed: Mar. 29, 2016

(65) Prior Publication Data

US 2016/0302788 A1 Oct. 20, 2016

Related U.S. Application Data

(60) Provisional application No. 62/149,829, filed on Apr. 20, 2015.

(51) Int. Cl.
| | |
|---|---|
| *A61B 17/06* | (2006.01) |
| *A61B 17/04* | (2006.01) |
| *A61L 17/08* | (2006.01) |
| *A61L 17/14* | (2006.01) |
| *A61F 2/00* | (2006.01) |

(Continued)

(52) U.S. Cl.
CPC .... *A61B 17/06166* (2013.01); *A61B 17/0469* (2013.01); *A61F 2/0045* (2013.01); *A61F 2/0063* (2013.01); *A61L 17/08* (2013.01); *A61L 17/12* (2013.01); *A61L 17/145* (2013.01); *A61B 2017/005* (2013.01); *A61B 2017/00955* (2013.01); *A61B 2017/00964* (2013.01); *A61B 2017/0619* (2013.01)

(58) Field of Classification Search
CPC ............................................... A61B 2017/0619
See application file for complete search history.

(56) References Cited

U.S. PATENT DOCUMENTS

| | | | | |
|---|---|---|---|---|
| 3,762,418 A | | 10/1973 | Wasson | |
| 5,417,700 A | * | 5/1995 | Egan | ................. A61B 17/0469 |
| | | | | 606/103 |

(Continued)

FOREIGN PATENT DOCUMENTS

| | | |
|---|---|---|
| CN | 101027013 A | 8/2007 |
| CN | 101044996 A | 10/2007 |

(Continued)

OTHER PUBLICATIONS

International Preliminary Report on Patentability for International Application No. PCT/US2016/025999, dated Nov. 2, 2017, 12 pages.

(Continued)

*Primary Examiner* — Shaun L David
(74) *Attorney, Agent, or Firm* — Brake Hughes Bellermann LLP

(57) ABSTRACT

This disclosure concerns suburethral and pelvic support structures which utilize tissue soldering materials instead of, or in addition to, traditional tissue anchors and suture knots. It further concerns methods of treating patients that includes implanting these structures and activating the tissue soldering materials to attach the structures to a tissue in the body of the patient.

20 Claims, 4 Drawing Sheets

(51) Int. Cl.
  *A61B 17/00* (2006.01)
  *A61L 17/12* (2006.01)

(56) References Cited

U.S. PATENT DOCUMENTS

| | | | |
|---|---|---|---|
| 5,509,923 | A | 4/1996 | Middleman et al. |
| 6,077,277 | A | 6/2000 | Mollenauer et al. |
| 6,368,343 | B1 | 4/2002 | Bonutti et al. |
| 7,166,570 | B2 | 1/2007 | Hunter et al. |
| 7,582,097 | B2 | 9/2009 | McRury et al. |
| 2002/0011508 | A1* | 1/2002 | Egan ............... A61B 17/06166 228/1.1 |
| 2002/0173821 | A1 | 11/2002 | Fenton et al. |
| 2004/0210282 | A1* | 10/2004 | Flock ............... A61L 27/50 606/228 |
| 2005/0277984 | A1* | 12/2005 | Long ............... A61B 17/06166 606/228 |
| 2008/0255611 | A1 | 10/2008 | Hunter et al. |
| 2010/0104608 | A1 | 4/2010 | Abuzaina et al. |
| 2011/0264139 | A1* | 10/2011 | Hunter ............. A61K 9/0024 606/228 |
| 2012/0191133 | A1 | 7/2012 | Ferree et al. |
| 2012/0245602 | A1 | 9/2012 | Glick et al. |
| 2013/0096611 | A1 | 4/2013 | Sullivan et al. |
| 2013/0158568 | A1* | 6/2013 | Kia ............... A61B 17/0469 606/144 |
| 2014/0257027 | A1 | 9/2014 | Brent et al. |
| 2014/0276910 | A1 | 9/2014 | Smith et al. |
| 2016/0174961 | A1 | 6/2016 | Callison et al. |
| 2016/0206308 | A1 | 7/2016 | Pereira et al. |
| 2016/0242763 | A1 | 8/2016 | Kia et al. |
| 2017/0290650 | A1* | 10/2017 | Levinson ............. A61F 2/0063 |

FOREIGN PATENT DOCUMENTS

| | | |
|---|---|---|
| CN | 101045000 A | 10/2007 |
| CN | 101045004 A | 10/2007 |
| CN | 101305926 A | 11/2008 |
| CN | 101466315 A | 6/2009 |
| CN | 101686831 A | 3/2010 |
| CN | 101861129 A | 10/2010 |
| CN | 101902974 A | 12/2010 |
| CN | 107106163 A | 8/2017 |
| CN | 107427298 A | 12/2017 |
| EP | 3244805 A1 | 11/2017 |
| WO | 2006084167 A1 | 8/2006 |
| WO | 2007089864 A2 | 8/2007 |
| WO | 2009086172 A2 | 7/2009 |
| WO | 2015050999 A1 | 4/2015 |
| WO | 2015089020 A1 | 6/2015 |
| WO | 2016171892 A1 | 10/2016 |

OTHER PUBLICATIONS

Invitation to Pay Additional Fees and Partial Search Report for International Application No. PCT/US2016/025999, dated Jun. 9, 2016, 10 pages.

International Search Report and Written Opinion for International Application No. PCT/US2016/025999, dated Aug. 18, 2016, 20 pages.

Summons to Attend Oral Proceedings for European Application No. 16716427.6, mailed Nov. 5, 2019, 5 pages.

* cited by examiner

FUSIBLE BIODEGRADABLE SUTURES UTILIZING TISSUE SOLDERING TECHNOLOGY

CROSS-REFERENCE TO RELATED APPLICATION

This application is a Nonprovisional of, and claims priority to, U.S. Patent Application No. 62/149,829, filed on Apr. 20, 2015, entitled "FUSIBLE BIODEGRADABLE SUTURES UTILIZING TISSUE SOLDERING TECHNOLOGY", which is incorporated by reference herein in its entirety.

TECHNICAL FIELD

This application relates to the field of medical devices. More particularly, the application is related to devices and methods for the treatment of pelvic organ prolapse and/or stress urinary incontinence.

BACKGROUND

A variety of medical procedures involve the implantation of sling-like structures to support soft tissues in and around the pelvis. For instance, genital prolapse or pelvic organ prolapse—the protrusion of the pelvic organs into or out of the vaginal canal—is frequently treated by a "Sacrocolpopexy" procedure involving the placement of a y-shaped mesh suspension structure to support the vagina. Sacrocolpopexy may involve open surgery, but is increasingly being done in a minimally-invasive fashion using laparoscopy. In a typical sacrocolpopexy procedure, the vagina/uterus is generally suspended to the sacral promontory with a mesh support structure that is secured to multiple pelvic structures by means of tissue anchors or knotted sutures. In fact, the Sacrocolpopexy procedure typically involves 14 suture knots, which can take 45 to 75 minutes to place in a typical laparoscopic Sacrocolpopexy procedure. If these knots are not tied precisely, they may fail, potentially resulting in failure of the procedure and/or undesirable movement of the support structure within the body. In some cases, robotic instruments have been used in an attempt to reduce the complexity and risk of knot failure in laparoscopic Sacrocolpopexy procedures, but a need still exists in the field for cost effective, simplified procedures for laparoscopic Sacrocolpopexy and for systems and devices that facilitate such procedures.

SUMMARY

The present invention, in its various aspects, addresses shortcomings in current laparoscopic sacrocolpopexy procedures by obviating the need for manually tied suture knots, instead utilizing a tissue soldering method that has been explored in other areas of medicine since the early 1990's, but has not found a successful application in this area of urology or women's health.

In one aspect, the present invention relates to a system for treating a patient that includes an implantable sling or mesh (which terms are used interchangeably to refer to any mesh, textile or polymer structure useful in suspending a portion of a prolapsed organ, particularly the supportive mesh structures described below) and a suture that includes a tissue soldering material (as defined more fully below). The system has a variety of optional features. For instance, in some cases, the soldering material is a coating on the surface of (part or all of) the suture, while in other cases the tissue soldering material is a microsphere that is (optionally) embedded in the suture, and in still other cases the suture itself is an extruded tissue soldering material. The system can also optionally include an energy source such as an LED light, a laser, or a radiofrequency electrode, which energy source is optionally insertable into the body of the patient. In some cases, the energy source is in or on a distal end of a device sized for insertion into the body such as a clamp, grasper, dissector, or a forceps. Alternatively, the energy source may be disposed within a suture capture device, which device preferably (but not necessarily) includes a housing defining a channel for the suture and a curved needle defining a lumen for the suture, which needle is slidably disposed within the housing and movable between first and second positions. In the first position, the distal end of the needle rests in a first portion of the housing, while in the second position, the needle extends in an arc such that the distal end of the needle is in a second portion of the housing; the energy source, in this instance, is located within or proximate to the second portion of the housing. The system according to this aspect, may be useful in medicine, more particularly in Sacrocolpopexy and/or laparoscopic medical procedures generally In another aspect, the present invention relates to a system for treating a patient that includes an implantable sling or mesh, a suture that includes a tissue soldering material, a device that includes (a) an energy source and (b) a housing defining a channel for the suture, and a curved needle slidably disposed within the housing and movable between first and second positions. In the first position, the distal end of the needle rests in a first portion of the housing, while in the second position, the needle extends in an arc such that the distal end of the needle is in a second portion of the housing; the energy source is located within or proximate to the second portion of the housing. As discussed above, the tissue soldering material may be a coating on a surface of the suture, it could be a microsphere that is optionally embedded within the suture, or the suture itself could be an extruded tissue soldering material. Other optional features are described above.

In another aspect, the present invention relates to a method of treating a patient that includes inserting a mesh support structure and a suture comprising an activatable tissue soldering material into the patient's body, extending at least a portion of the suture through the mesh structure and a tissue, thereby drawing the mesh and tissue together, then contacting first and second ends of the suture to form a loop and applying energy to the first and second ends where they cross, activating the tissue soldering material and securing the ends of the suture to one another. In some cases, the mesh is positioned proximate to the vagina and/or the suture is extended through the tissue and the mesh using a laparoscopic surgical instrument, which instrument is also optionally used to apply energy to the suture and which instrument is optionally selected from the group consisting of a clamp, a grasper, a dissector and a forceps.

BRIEF DESCRIPTION OF THE FIGURE

Aspects of the invention are described below with reference to the following drawings in which like numerals reference like elements, and wherein.

Unless otherwise provided in the following specification, the drawings are not necessarily to scale, with emphasis being placed on illustration of the principles of the invention.

DETAILED DESCRIPTION

The systems and methods of the present invention utilize "tissue soldering materials," which term refers generally to materials that facilitate adhesion between implanted materials and patient tissues and are preferably (though not necessarily) provided in an inert or unreactive state and transition into a reactive state (again preferably, though not necessarily) through contact with or exposure to a stimulus. The stimulus can be one that exists generally within the body, e.g. water found in aqueous bodily fluids, or it can be externally applied by a user (e.g. light, heat, radio frequency, radiation, or application of an electric field). For instance, the various systems and methods described below can use protein-based tissue soldering materials and, optionally, these protein-based materials include a chromophore or photosensitizers.

Figure 1A:
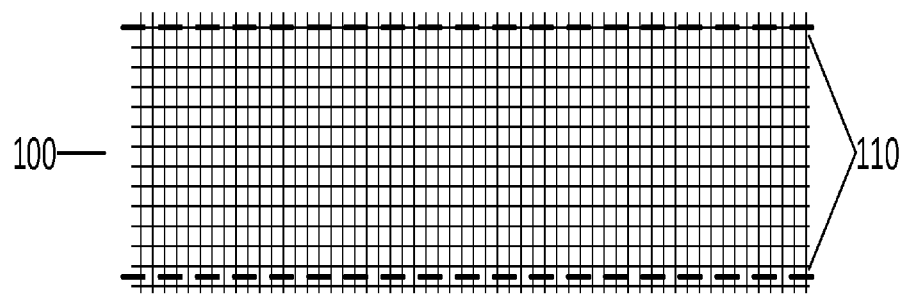
FIGS. 1A and 1B show schematic views of mesh incorporating tissue soldering materials according to certain embodiments of the invention.
Figure 1B:
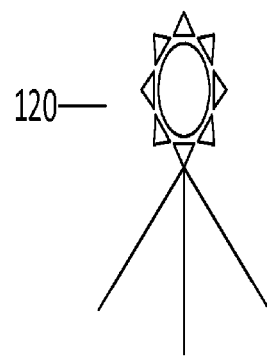
Figure 1B:
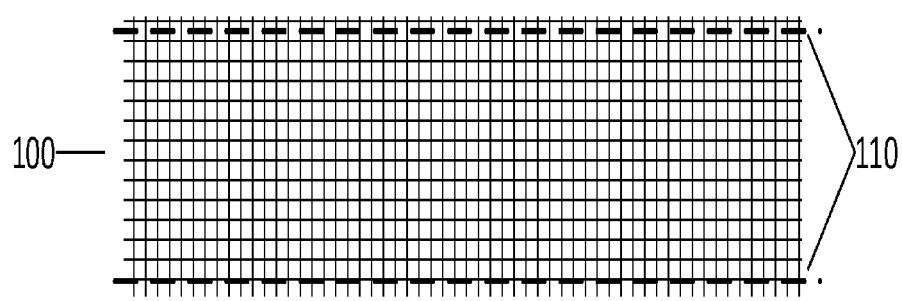
Figure 2A:
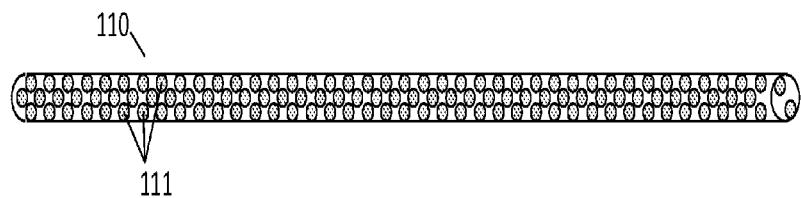
FIGS. 2A and 2B show schematic depictions of sutures incorporating tissue soldering materials according to certain embodiments of the present invention.
Figure 2B:
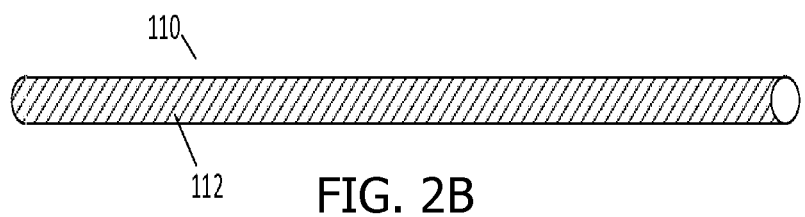

Turning to FIG. 1, an exemplary sling 100 according to the present invention includes at least one suture 110 that incorporates a tissue-based soldering material. The tissue soldering material is incorporated into the suture 110 in any suitable manner, including coating the suture 110 (which suture may be braided or a metal or polymer monofilament, or bioabsobable suture material such as Polyglactin, Poliglecaprone, Polydioxanone, chromic gut, etc. . . . ) with the tissue soldering material as shown in FIG. 2B, embedding tissue solder material micro- or nanospheres within the suture 110 as shown in FIG. 2A, or forming part or all of the suture from tissue solder material 112, e.g. by extrusion. An exemplary listing of means by which tissue soldering material is incorporated within suture 110 is presented in Table 1, below:

TABLE 1

SUTURE ARRANGEMENTS

Suture is made entirely of solder material and is bio-absorbable.
Suture is coated with solder material.
    Suture is made of a bio-absorbable material and bio-absorbs after the solder.
    Suture is made of a bio-compatible material that does not bio-absorb.
    Solder includes a non-uniform coating:
        Coating may be thicker in some spots and thinner in others, and optionally forms a pattern or texture.
        Coating may form a protrusion or barb to provide an additional level of mechanical attachment.
    Solder can be coated onto the suture with an intermediate layers such as styrene isoprene TABLE 1-continued

SUTURE ARRANGEMENTS butadiene block copolymers ("SIBS") in a manner analogous to that employed in drug eluting stents.
Reactive micro- or nanoparticles such as superparamagnetic iron oxide nanoparticles ("SPIONS") or gold nanorods that react to light at a wavelength that passes through tissue are embedded within the suture so that bonds may be created within the tissue.
Suture can be any geometric shape - round, square, ribbon, etc.

In the embodiment shown in the figures, the sling 100 includes a mesh material and the suture 110 is threaded through the sling 100 and a body tissue to which the sling 100 will be attached. Thereafter, in these exemplary embodiments, external, energy is applied to the suture 110 by means of an external energy source 120. The application of energy with the external source 120 activates the tissue solder, thereby causing or facilitating attachment of the suture, and consequently the sling, to a body tissue. The energy source 120 can be any suitable source of energy, but is preferably one or more of a laser, light-emitting diode, ultrasound transducer, radiation or radiofrequency electrode.

FIG. 1 shows the suture as a running stitch without knots or loops, though in some cases tissue soldering is combined with knotted and/or looped sutures 110. In some cases, such as the one shown in FIG. 1B, the external source 120 is positioned to one side of the mesh 100 and sutures 110, and energy is applied only to one side of the mesh 100; thus activated, the sutures 110 are generally able to drive adhesion between the energized side of the sling 100 and an adjacent tissue, though in cases where the suture 100 incorporates one or more tissue solder nanoparticles 111, it may be capable of adhering to tissue on both sides of the sling 100.

Figure 2C:
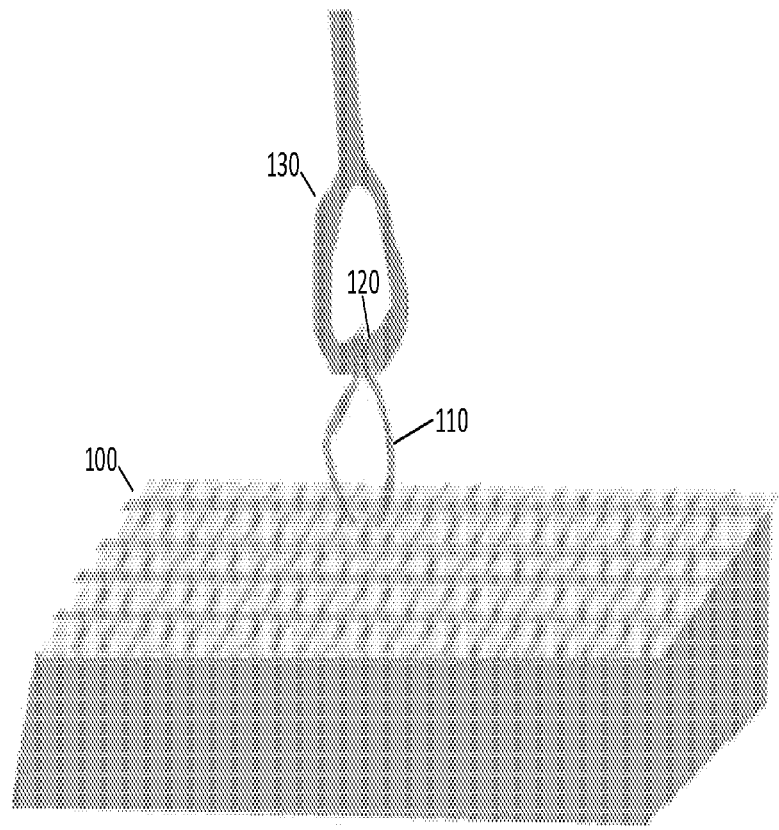
FIG. 2C shows a schematic depiction of a mesh and a tissue soldering device used in according with certain embodiments of the present invention.

In other cases, the suture 110 is looped and the free ends are bonded to one another by means of a clamp-like device 130, as shown in FIG. 2C. The clamp includes an energy source 120 at one or both ends thereof. In use, the free ends of the suture 110 are brought together, for instance by means of the clamp device 130 itself, and the energy source 120 is activated, thereby adhering the two free ends to one another. The clamp device 130 is preferably shaped and sized to limit or prevent the application of energy to the tissue. Alternatively, the energy source 120 is integrated into a laparoscopic device such as a grasper or dissector. In these instances, a fiber optic light path is preferably integrated into the grasper head to deliver laser or led energy to seal or fuse the ends together.

Figure 3:
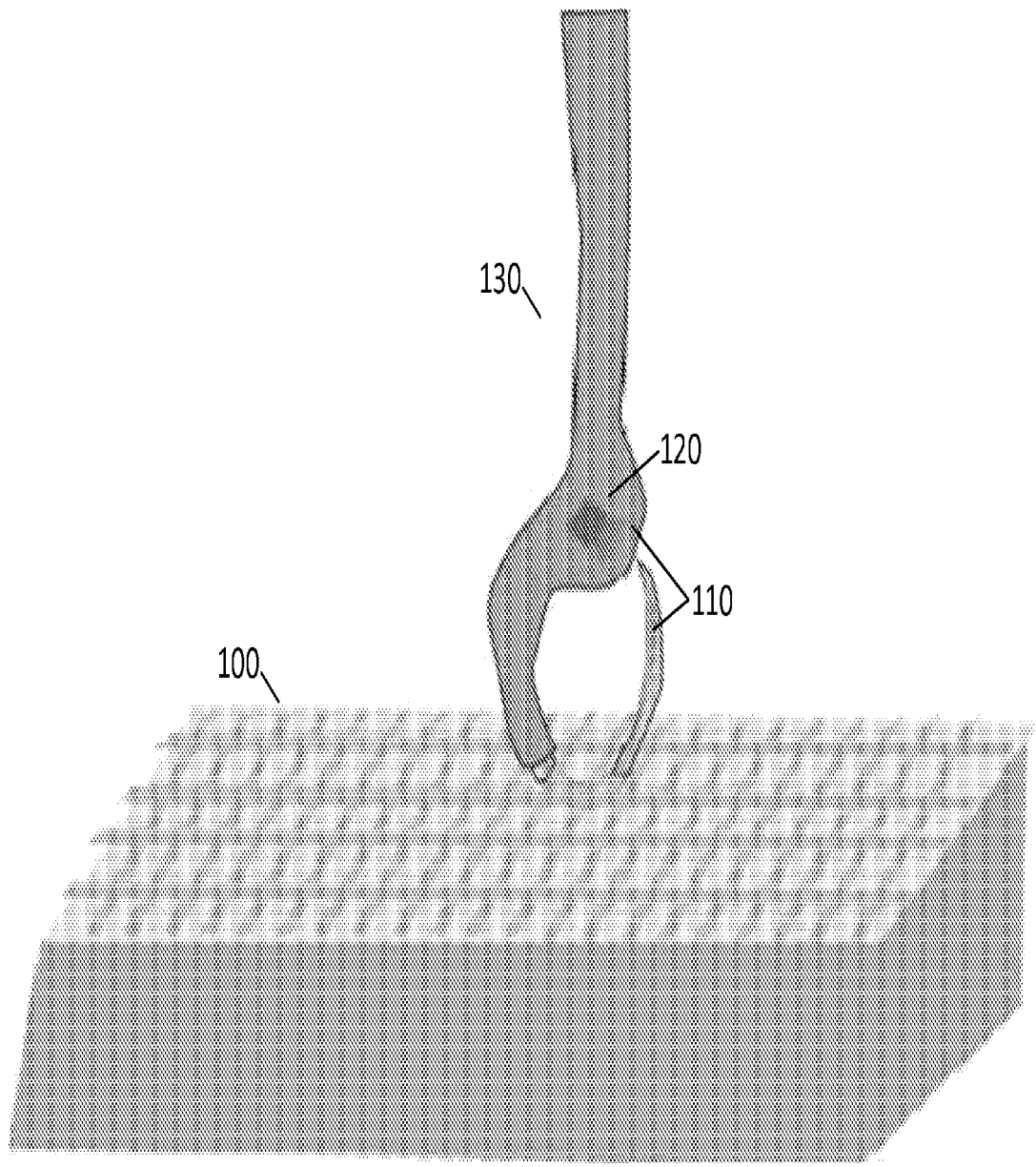
FIG. 3 shows a schematic depiction of a sling and a tissue soldering device used in according with certain embodiments of the present invention.
Figure 4A:
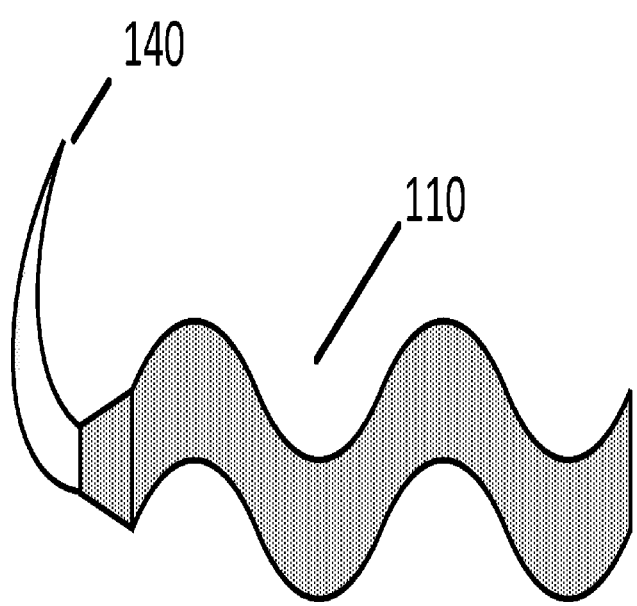
FIG. 4A-D show, in schematic form, several steps in the deployment of a suture and mesh according to certain embodiments of the present invention.
Figure 4C:
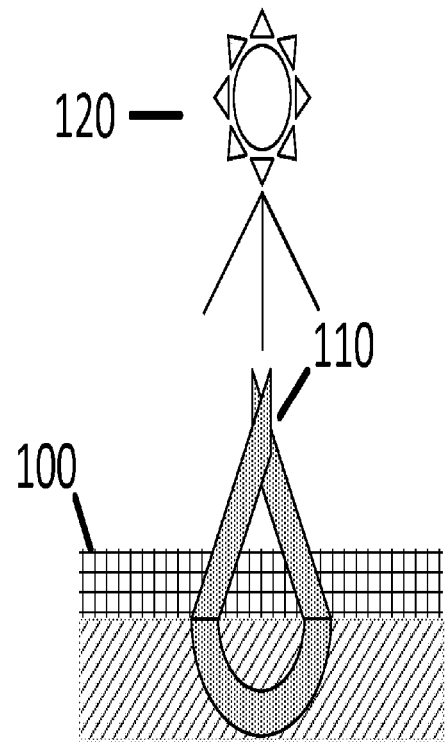
Figure 4B:
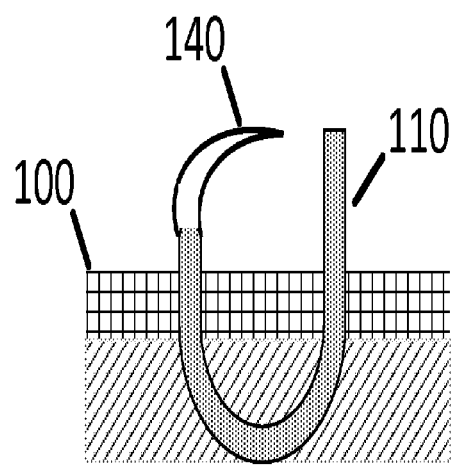
Figure 4D:
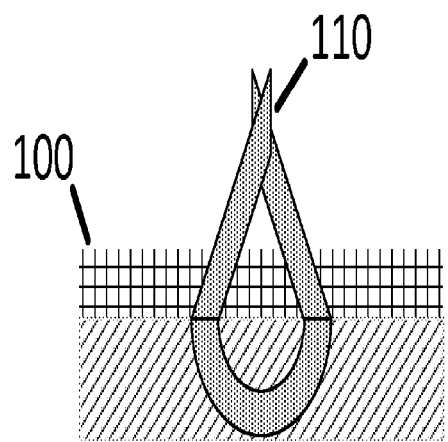

Turning to FIG. 3, in some cases a single free end of the suture 110 is inserted through the mesh 100 and the tissue, and is looped back upon itself for adhesion using a suture capturing device 130 that includes an energy source 120. The suture capture device 130 preferably includes a distal curved portion in which a curved needle 140 is slidably disposed; when deployed, the curved needle 140 extends through the mesh 100 and/or tissue such that a distal tip of the curved needle 140 is closely apposed to, or inserted within, a portion of the suture capture device 130 housing the energy source 120. After energy is applied, the free end of the suture 110 is attached to the suture, and the device 130 is retracted over the suture 110, which is then optionally cut to length.

Systems and methods of the present invention can be used in any procedure where sutures or tissue anchors are currently used with difficulty, including without limitation ureteral or urethral anastomosis, sacrocolpopexy, closure of the peritoneum, port closure, etc. The systems and methods of the present invention offer several advantages over suturing or tissue anchoring methods currently used in the art, including reducing the time and difficulty of securing sutures for support structure placement. In addition, insofar as less user skill is required to use energy delivery devices such as those described above versus manually tying knots, the systems and methods of the present invention can reduce time and costs associated with training users to perform support structure placement procedures.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for treating a patient, comprising:
   an implantable mesh including a longitudinal axis extending between a first end portion and a second end portion of the mesh, the implantable mesh having a first side edge and a second side edge opposite the first side edge; and
   a bioabsorbable suture including a tissue soldering material, the suture being coupled to the mesh and extending substantially linearly and parallel to the first side edge, the suture extending from the first end portion to the second end portion, the suture configured to be in a first state and in a second state, different than the first state, the second state being activated in response to contact or exposure to a stimulus thereby causing the suture to adhere to a bodily tissue of the patient the tissue soldering material includes a non-uniform coating that forms a texture configured to provide mechanical attachment to bodily tissue.

2. The system of claim 1, wherein the coating is on a surface of the suture.

3. The system of claim 1, wherein the tissue soldering material includes a microsphere.

4. The system of claim 3, wherein the microsphere is embedded in the suture.

5. The system of claim 1 wherein the suture is an extruded tissue soldering material.

6. The system of claim 1, further comprising an energy source.

7. The system of claim 6, wherein the energy source is one of an LED light, a laser, a radiofrequency electrode.

8. The system of claim 6, wherein the energy source is insertable into a body of the patient.

9. The system of claim 8, wherein the energy source is disposed within or on a distal end of a device selected from the group consisting of a clamp, grasper, dissector, and a forceps, wherein the device is sized to be at least partially inserted into the body of a patient.

10. The system of claim 8, wherein the energy source is disposed within a suture capture device.

11. The system of claim 1, wherein the mesh includes a first side portion and a second side portion, the suture extends along the first side portion and the second side portion of the mesh.

12. The system of claim 1, wherein the suture extends substantially parallel to the longitudinal axis.

13. A system for treating a patient, comprising:
   an implantable mesh including a longitudinal axis extending between a first end portion and a second end portion of the mesh; and
   a bioabsorbable suture including a tissue soldering material, the suture being coupled to the mesh, the suture extending substantially linearly from the first end portion to the second end portion, the suture configured to be in a first state and in a second state, different than the first state, the second state being activated in response to contact or exposure to a stimulus such that the suture adheres to a bodily tissue of the patient, the tissue soldering material includes a non-uniform coating that forms a texture configured to help provide mechanical attachment to bodily tissue;
   a device including an energy source.

14. The system of claim 13, wherein the coating is on a surface of the suture.

15. The system of claim 13, wherein the tissue soldering material includes a microsphere.

16. The system of claim 15, wherein the microsphere is embedded in the suture.

17. The system of claim 13 wherein the suture is an extruded tissue soldering material.

18. The system of claim 13, wherein the mesh includes a first side portion and a second side portion, the suture extends along the first side portion and the second side portion of the mesh.

19. The system of claim 13, wherein the suture extends substantially parallel to the longitudinal axis.

20. The system of claim 13, wherein the coating includes a first portion and a second portion, the first portion being thinner than the second portion.

* * * * *